US 8,281,926 B2

(12) United States Patent
Messerschmidt et al.

(10) Patent No.: US 8,281,926 B2
(45) Date of Patent: Oct. 9, 2012

(54) PACKAGE COMPRISING HOLISTIC CODING SYSTEM

(75) Inventors: Andreas Stephanus Lambertus Messerschmidt, Bad Soden (DE); Susanne Will, Schwalbach (DE)

(73) Assignee: The Procter and Gamble Company, Cincinnati, OH (US)

( * ) Notice: Subject to any disclaimer, the term of this patent is extended or adjusted under 35 U.S.C. 154(b) by 621 days.

(21) Appl. No.: 11/811,037

(22) Filed: Jun. 8, 2007

(65) Prior Publication Data
US 2008/0000793 A1 Jan. 3, 2008

(30) Foreign Application Priority Data
Jun. 29, 2006 (EP) .................................... 06116276

(51) Int. Cl.
*B65D 1/34* (2006.01)
*B65D 6/04* (2006.01)

(52) U.S. Cl. .................. 206/459.5; 206/459.1; 206/438; 206/439; 206/440; 206/812

(58) Field of Classification Search ............... 206/459.1, 206/459.5, 438–440, 812, 494
See application file for complete search history.

(56) References Cited

U.S. PATENT DOCUMENTS

| | | | |
|---|---|---|---|
| 6,454,095 B1 | 9/2002 | Brisebois et al. | |
| 6,520,330 B1 * | 2/2003 | Batra | 206/494 |
| 6,601,705 B2 * | 8/2003 | Molina et al. | 206/494 |
| 6,685,020 B2 | 2/2004 | Briseboi et al. | |
| 6,698,928 B2 * | 3/2004 | Miller | 383/205 |
| 2003/0106825 A1 | 6/2003 | Molina et al. | |
| 2003/0127352 A1 * | 7/2003 | Buschkiel et al. | 206/494 |
| 2003/0130632 A1 * | 7/2003 | Costea et al. | 604/362 |
| 2004/0050738 A1 * | 3/2004 | Molina et al. | 206/440 |
| 2004/0102748 A1 | 5/2004 | Hirotsu | |
| 2004/0238393 A1 | 12/2004 | Ohi et al. | |
| 2005/0145523 A1 | 7/2005 | Zander et al. | |
| 2005/0154365 A1 | 7/2005 | Zander et al. | |
| 2007/0144937 A1 * | 6/2007 | Gilroy | 206/776 |

OTHER PUBLICATIONS

PCT International Search Report dated Apr. 12, 2007.

* cited by examiner

*Primary Examiner* — J. Gregory Pickett
*Assistant Examiner* — Blaine Neway
(74) *Attorney, Agent, or Firm* — Megan C. Hymore; Brian M. Bolam; David M. Weirich

(57) ABSTRACT

A package for household articles provided with a holistic coding system. The coding system allows consumers to select the articles required for their needs without confusion. The coding system includes first coding elements on the dispensing means of package and second coding elements on the articles contained in the package.

15 Claims, 1 Drawing Sheet

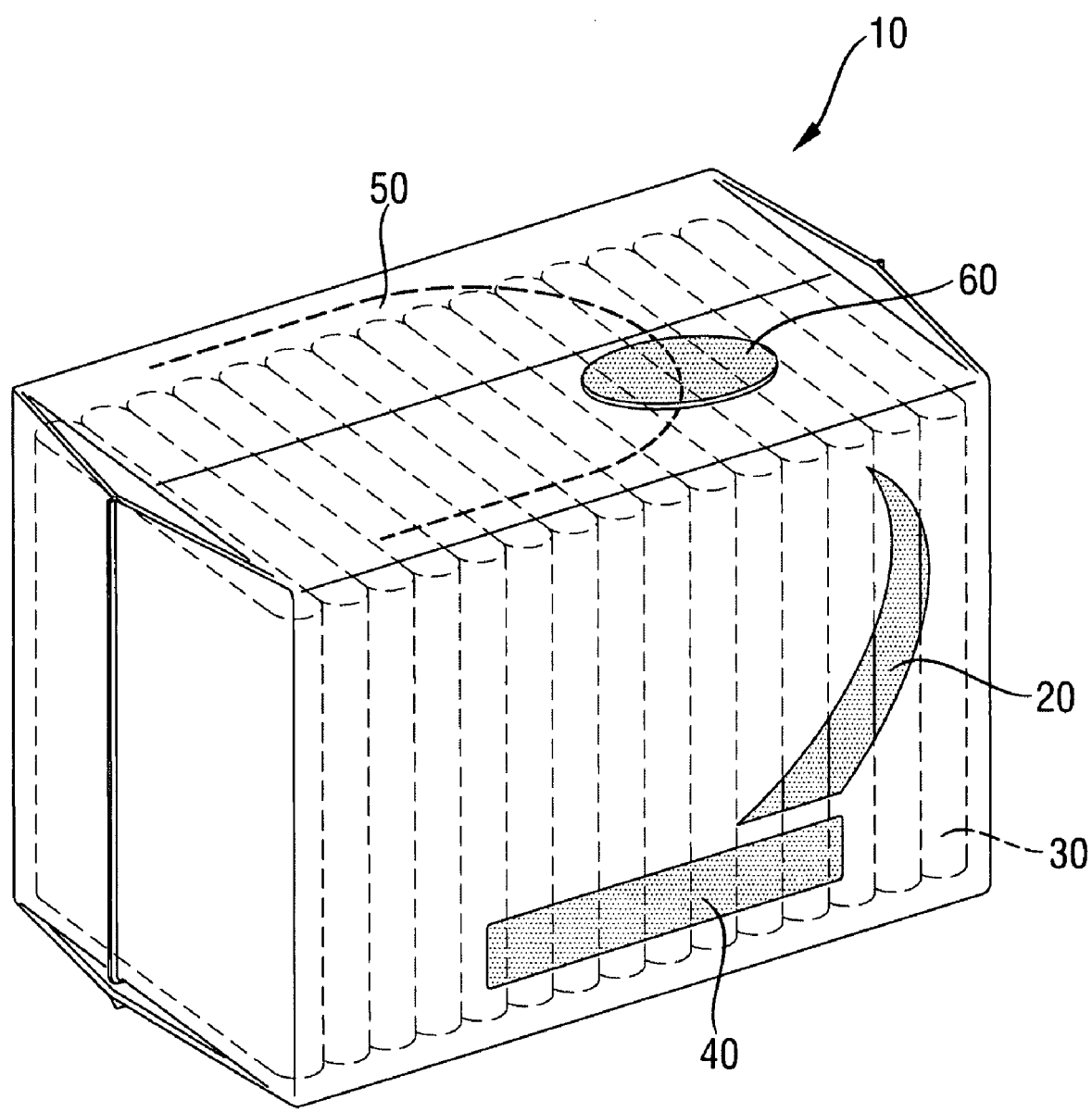

PACKAGE COMPRISING HOLISTIC CODING SYSTEM

FIELD OF THE INVENTION

A package for household articles is claimed, which package is provided with a holistic coding system. The coding system allows consumers to select the articles required for their needs without confusion. The coding system includes first coding elements on the dispensing means of package and second coding elements on the articles contained in the package.

BACKGROUND OF THE INVENTION

Household articles, especially hygiene articles, are available in many sizes and varieties from many manufacturers. Especially in the field of absorbent articles, the consumer is offered a multitude of different sizes, absorbencies and other performance features. Further, absorbent articles, such as sanitary napkins, are more and more tailored towards certain specialized end uses such as overnight pads, incontinence pads and the like. As said above, the variety of offers to the consumer is further increased by the fact that there are numerous producers and brands competing in this field, which multiplies the amount of articles presented in the shelves of the retailers to the consumer. All this variety is of significant benefit to the consumers as it more and more reflects all their individual needs, but on the other hand, the amount of different articles in different packaging configurations also can lead to confusion. Consumers are more and more likely to purchase an article which is not the one they were actually planning to purchase because of loss of orientation in an ever increasing amount of offers to them. Of course, such experiences provide consumers with frustration and potentially to the wrong conclusion that the variety of articles offered by the industry is not to serve them but more to confuse them.

Therefore, it would be desirable to better present household articles to the consumer such that the consumer can easily recognize the product and its performance features.

Furthermore, it would be desirable to present household articles to the consumer such that the consumer can easily select the right articles for his or her needs such that the time he or she has to spend at the shelves of those articles is reduced.

SUMMARY OF THE INVENTION

A package containing at least one household article, the package being made of a package material. The package has an outer surface and an interior, the interior enclosing the household article. The package is provided with a consumer-noticeable coding system. The coding system includes first coding elements on the dispensing means of package and second coding elements on the household article, wherein the second coding elements are consumer-noticeable through the closed package.

BRIEF DESCRIPTION OF THE DRAWINGS

FIG. 1 is a perspective view of an exemplary execution of the present invention.

DETAILED DESCRIPTION OF THE INVENTION

"Household articles" herein refers to various kinds of articles needed on a daily or at least frequent basis in the household. The household articles herein may be discrete articles, packaged in individual wrappers. Examples of household articles are detergent tablets or liquitabs, hygiene articles, or cosmetic articles such as beauty care items.

"Hygiene articles" as used herein refers to products of personal hygienic care, such as disposable articles. Typical disposable hygiene articles are moistened and non-moistened wipes or pads, or absorbent articles like infant diapers, sanitary napkins, panty liners, breast pads, tampons and the like.

"Package" as used herein refers to wrappers or containers for household articles. The package according to the present invention is typically made from polymeric film like polyethylene (PE), polypropylene (PP), laminates, woven webs or fabrics. Polymeric films also include blown or cast film materials in a blend of low density polyethylene (LDPE), linear low density polyethylene (LLDPE), metallocene PE blends (metPE), ethylene vinyl acetate, Surlyn®, polyethylene terephthalate (PET), mono- and biaxially oriented polypropylene (M/BoPP) and nylon. Woven and non-woven webs can be formed from monocomponent fibres, bicomponent fibres, multiconstituent fibres, capillary channel fibres and the like. A polymeric film can be two or more films laminated together. A polymeric film can be pigmented. A polymeric film can be clear or opaque. The package encloses the household articles in a hygienically protective manner. The household articles are typically arranged in one or more stacks inside the package. In alternative embodiments the package can be made of carton/cardboard material.

"Individual wrapper" or "wrapper" as used herein denominates an individual container (e.g. envelope, sachet, etc.) for an article or a certain amount of solid or liquid substance. The individual wrappers are in some embodiments herein used for packing articles or substances individually inside the package of the present invention. Such wrappers may have any suitable size and shape and may be constructed from any suitable material. An example is a pouch wrapper as currently on the market for ALWAYS® sanitary napkins as marketed by the Procter & Gamble Company of Cincinnati, Ohio. This wrapper is a film being tri-folded such that the two end portions overlap each other. The overlapping portions are joined by an adhesive strip. On the sides this wrapper is closed by crimp lines.

"Holistic coding system" as used herein refers to consumer-noticeable information being present on the package and on the articles contained in the package. By the holistic coding system, the consumer is enabled to properly select the household articles he or she actually was planning to purchase in a fast and convenient matter without having to extensively study the package. The consumer-noticeable information is provided by the first and second coding elements.

"Coding elements" as used herein refers to consumer-noticeable colors or indicia, such as letters, symbols, lines, patterns, ornamental designs, pictures, script, characters and the like as well as combinations thereof. The coding elements may be present in various regions of the package and the articles contained in the package. The coding elements herein typically refer to product properties. Such product properties are, for example, certain levels of absorbency, dryness, softness, size, calliper, product shape (like thong shape) or suggested product usage like day or night product and the like.

"Consumer-noticeable" as used herein means that the coding elements are noticeable to the consumer visually or via tactile sensations without having to open the package. This includes that the coding elements have to be sized and shaped to be appropriately noticeable, e.g. by the naked eye from a distance of at least 1 meter. Examples of coding elements are colored areas on the outer surface of the package material, colored reclosure patches for closing the dispensing opening of the package, symbols or letters, which are placed on prominent regions of the package or the household articles or combinations thereof. Tactile coding elements include embossments, notches and the like. Also combinations of visual and tactile coding elements are possible.

The "first coding elements" are present on the dispensing mechanism, such as the dispensing flap or the closing means for the dispensing flap. Specifically an adhesive strip for reclosing the dispensing opening can be colored and/or be provided with indicia and/or have a shape resembling an indicium. Another example of the dispensing mechanism carrying first coding elements is a pouch with a drawable ribbon or string as closure for the dispensing opening. This ribbon can be colored and/or can be provided with indicia. A specific example is a colored adhesive strip for reclosing an opened dispensing flap.

Examples for the "second coding elements" are colored areas or indicia on the household articles, or, in case the articles are individually packed, on the outsides of the individual wrappers of the articles. Another example for the second coding elements is a colored adhesive strip for reclosing the individual wrapper of a household article contained in the package according to the present invention. The second coding elements are, although being inside the package, noticeable to the consumer even when the package is closed. An exemplary execution is a package having a window through which the consumer can visually notice the articles contained in the package and colors and/or indicia present on them. An alternative execution of the second coding elements is that the articles contained in the package are visible through a window in the package material, which window is transparent but pigmented, i.e. colored. The interaction between the color of the articles contained in the package, or their individual wrapper, and the color of the window in this embodiment resembles the coding element, e.g. the specific coding color. In a specific example, a white tampon is perceived through a yellow window as being yellow. In another exemplary execution, a yellow tampon is perceived through a blue window as being green.

Optionally, the package herein can be provided with "third coding elements". The third coding elements are present on the household products contained in the package but are not necessarily consumer-noticeable when the package is closed. An example of a third coding element is the adhesive strip for closing the above-described ALWAYS® wrapper, which adhesive strip is colored and/or provided with indicia. Further, the adhesive strip can itself be shaped to resemble an indicium. Another example for the third coding elements is a tear tape for opening an individual wrapper of a hygiene article in the package, such as a tampon wrapper, which tear tape is provided with colors and/or indicia. In another embodiment, the removal string of a tampon is colored for providing a third coding element. In further embodiments the third coding elements are present on the hygiene article itself, such as on the topsheet and/or on the backsheet of a sanitary napkin. By using transparent material for making the individual wrapper these coding elements become consumer-noticeable prior to opening the wrapper.

Further, the package herein can be provided with "fourth coding elements", which are present on the outside surface of the package. Examples include colored areas and/or indicia on a prominent region of the outer package surface.

It may be desirable in certain embodiments that the various coding elements herein are identical. This means that all the coding elements should resemble the same color and/or the same indicia. By "identical" it is not excluded herein that the actual size of the coding elements, thus the size of a colored region and/or the indicia, may be different. The "same color" herein includes also darker or lighter shadings of a certain color, such as a darker and a lighter green.

In an exemplary embodiment of the present invention, as shown in FIG. 1, package (10) made of clear polymeric film is printed to be opaque with the exception of a non-opaque area forming a window (20). The window (20) allows consumers to visually notice the articles (30) in the package (10). The package (10) is provided with a colored region (40) on its outside. Further, the package has a reclosable dispensing flap (50). The dispensing flap (50) is provided with an adhesive tape (60) for reclosure, which has the same color as the colored region (40). Finally, the individual wrappers of the articles (30) contained in the package (10) have the same color as the colored region (40) and the adhesive tape (60), which can be noticed through the window (20). Such an execution provides the possibility to correlate for instance certain colors with certain features of the articles (30) in the package (10), such as their absorbency capacity.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package containing at least one hygiene article;
    the package being made of a package material;
    the package having an outer surface, a dispensing flap, a reclosable adhesive tape, a pigmented, non-opaque window having a color, and an interior, the interior enclosing the at least one hygiene article;
    the package having a consumer-noticeable first coding element having a color on the dispensing flap of the package; and
    the at least one hygiene article having a consumer-noticeable second coding element having a color;
    wherein, the interaction between the color of the pigmented, non-opaque window and the color of the consumer-noticeable second coding element provides a color that resembles the color of the consumer-noticeable first coding element; and
    wherein the at least one hygiene article is perceived through the window as having a color that is different from both the color of the at least one hygiene article as well as the color of the window.

2. The package of claim 1, wherein the consumer-noticeable first and second coding elements are indicia.

3. The package of claim 2, wherein the indicia are selected from letters, symbols, lines, patterns, ornamental designs, pictures, script, characters as well as combinations thereof.

4. The package of claim 1, wherein the color of the consumer-noticeable first coding element differs from the color of the consumer-noticeable second coding element.

5. The package of claim 1, wherein the color of the pigmented, non-opaque window is yellow.

6. The package of claim 1, wherein the color of the pigmented, non-opaque window is blue.

7. The package of claim 1, wherein the color of the pigmented, non-opaque window is green.

8. The package of claim 1, wherein the pigmented, non-opaque window is transparent.

9. A package containing at least one hygiene article;
the package being made of a package material;
the package having an outer surface, a dispensing flap, a reclosable adhesive tape, a pigmented, transparent window having a color, and an interior, the interior enclosing the at least one hygiene article;
the package having a consumer-noticeable first coding element having a color on the dispensing flap of the package; and
the at least one hygiene article having a consumer-noticeable second coding element having a color;
wherein, the interaction between the color of the pigmented, transparent window and the color of the consumer-noticeable second coding element provides a color that resembles the color of the consumer-noticeable first coding element; and
wherein the at least one hygiene article is perceived through the window as having a color that is different from both the color of the at least one hygiene article as well as the color of the window.

10. The package of claim 9, wherein the consumer-noticeable first and second coding elements are indicia.

11. The package of claim 9, wherein the indicia are selected from letters, symbols, lines, patterns, ornamental designs, pictures, script, characters as well as combinations thereof.

12. The package of claim 9, wherein the color of the consumer-noticeable first coding element differs from the color of the consumer-noticeable second coding element.

13. The package of claim 9, wherein the color of the pigmented, non-opaque window is yellow.

14. The package of claim 9, wherein the color of the pigmented, non-opaque window is blue.

15. The package of claim 9, wherein the color of the pigmented, non-opaque window is green.

* * * * *